United States Patent
Wolfe

(10) Patent No.: US 9,693,779 B2
(45) Date of Patent: Jul. 4, 2017

(54) LIGATOR FOR USE WITH AN ENDOSCOPE

(71) Applicant: Endochoice, Inc., Alpharetta, GA (US)

(72) Inventor: Justin Wolfe, Alpharetta, GA (US)

(73) Assignee: EndoChoice, Inc., Alpharetta, GA (US)

( * ) Notice: Subject to any disclaimer, the term of this patent is extended or adjusted under 35 U.S.C. 154(b) by 111 days.

(21) Appl. No.: 14/737,733

(22) Filed: Jun. 12, 2015

(65) Prior Publication Data

US 2016/0361066 A1    Dec. 15, 2016

(51) Int. Cl.
*A61B 17/10* (2006.01)
*A61B 17/12* (2006.01)
*A61B 1/00* (2006.01)
*A61B 17/00* (2006.01)

(52) U.S. Cl.
CPC .... *A61B 17/12013* (2013.01); *A61B 1/00087* (2013.01); *A61B 2017/00296* (2013.01); *A61B 2017/00407* (2013.01); *A61B 2017/00778* (2013.01); *A61B 2017/00818* (2013.01); *A61B 2017/12018* (2013.01)

(58) Field of Classification Search
CPC .... A61B 17/12013; A61B 2017/12018; A61B 2019/4815; A61B 2017/00296
USPC ................ 606/139, 140, 144, 151, 157, 228
See application file for complete search history.

(56) References Cited

U.S. PATENT DOCUMENTS

| | | | |
|---|---|---|---|
| 5,320,630 A | 6/1994 | Ahmed | |
| 5,398,844 A | 3/1995 | Zaskavsky | |
| 6,051,003 A | 4/2000 | Chu | |
| 6,059,798 A | 5/2000 | Tolkoff | |
| 6,149,659 A | 11/2000 | Ahmed | |
| 6,235,040 B1 | 5/2001 | Chu | |
| 8,845,516 B2 * | 9/2014 | Chami | ............ A61B 17/12013 600/104 |
| 8,974,474 B2 * | 3/2015 | Kamler | ............ A61B 17/12013 606/140 |

FOREIGN PATENT DOCUMENTS

WO    WO97/16120    5/1997
WO    WO0245595    6/2002

* cited by examiner

*Primary Examiner* — Vy Bui
(74) *Attorney, Agent, or Firm* — Thomas | Horstemeyer, LLP

(57) ABSTRACT

In one embodiment, a ligator adapted for use with an endoscope includes a ligator body adapted to mount to a body of the endoscope, a barrel adapted to mount to a distal tip of a shaft of the endoscope, the barrel supporting multiple elastic bands that can be sequentially deployed onto internal tissue, and an activation mechanism supported by the ligator body, the activation mechanism including a rotatable activation knob, a rotatable cord winding ring, an activation cord, and a stop element that limits rotation of the activation knob to rotation between a start position and an end position beyond which no further rotation is possible.

16 Claims, 5 Drawing Sheets

LIGATOR FOR USE WITH AN ENDOSCOPE

BACKGROUND

Tissue ligation is a surgical or medical procedure in which an anatomical structure, such as a blood vessel, is tied off or constricted so as to limit or prevent flow through or to part of the structure. For example, varicose veins in the gullet or a duodenal diverticulum can be ligated by applying small elastic bands to the vein using an endoscope while observing the vein through the optics of the endoscope.

It can be difficult for a surgeon to both position an endoscope at the ligation site and deploy elastic bands onto tissue. It is, therefore, common practice for an assistant to activate release of the elastic bands while the surgeon maneuvers the endoscope. It would be desirable to have an apparatus that would enable the surgeon to both maneuver the endoscope and activate release of the elastic bands without difficulty.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an apparatus that would enable a surgeon to both maneuver an endoscope and activate release of elastic bands from the endoscope without difficulty. Disclosed herein are ligators that are designed to facilitate such operation. As described below, the ligators are adapted to securely mount to an endoscope and comprise an activation mechanism that can be operated by the surgeon to cause the deployment of individual elastic bands from a barrel mounted to the distal tip of the endoscope shaft. The activation mechanism comprises an activation knob that can be rotated from a start position to an end position beyond which further rotation is not possible because of the presence of a stop element. When the activation knob reaches the end position, the activation mechanism causes deployment of a single elastic band from the barrel at the tip of the endoscope shaft. The activation knob can then return to the start position under the force of an internal spring so that it is ready to deploy the next elastic band, if necessary. In some embodiments, the elastic bands comprise molded synthetic elastomer bands that do not comprise the proteins to which some patients are allergic.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
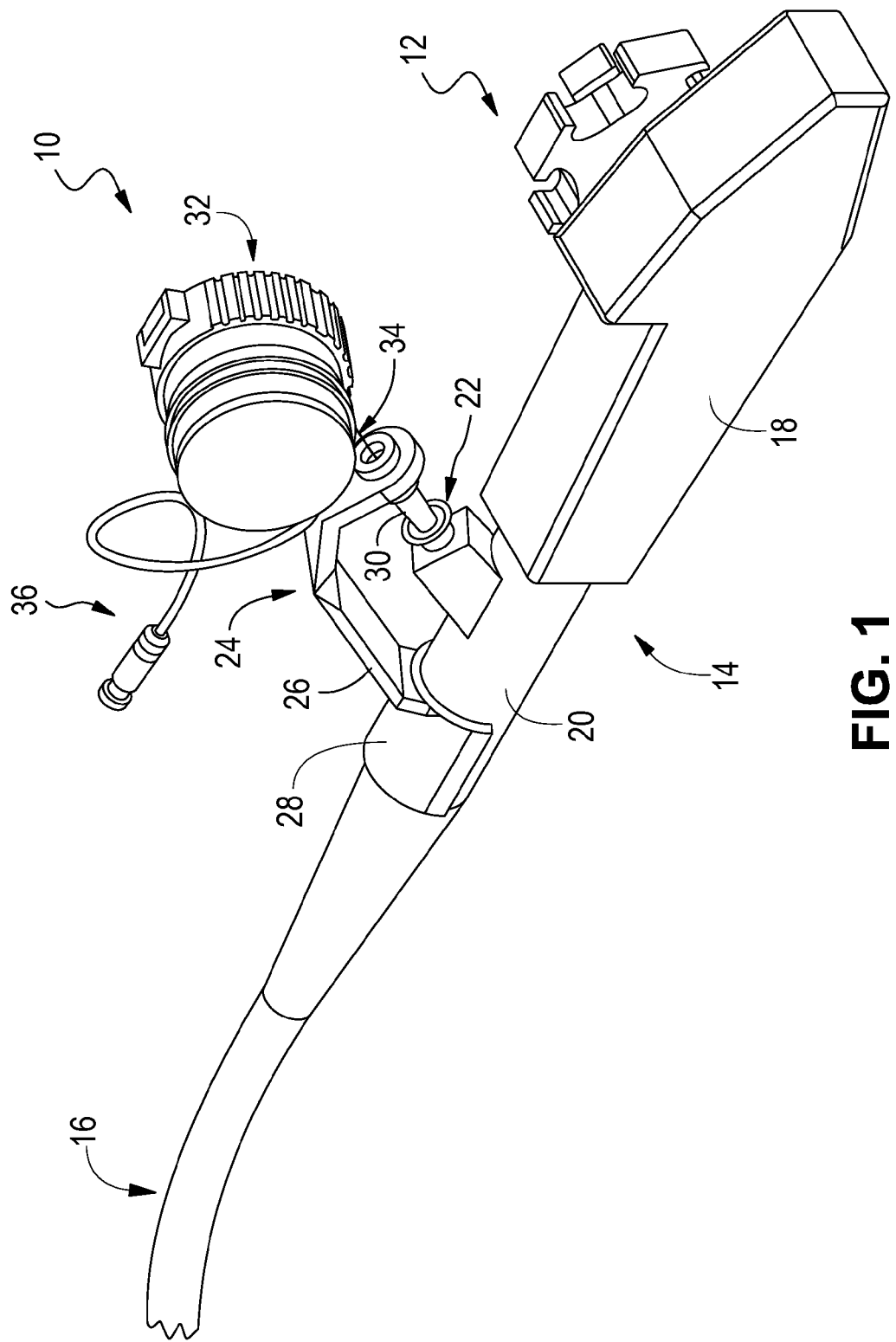
FIG. 1 is a perspective view of an embodiment of a ligator that is shown mounted to an endoscope.

FIG. 1 illustrates an embodiment of an activation portion of a ligator 10 mounted to an endoscope 12. As indicated in the figure, the endoscope 12 comprises a body 14 that can be gripped by the surgeon and an elongated flexible shaft 16 that can be inserted into a cavity of a patient for the purpose of ligating internal tissue. Although not depicted in FIG. 1, the ligator 10 further includes a barrel that can be mounted to the distal tip of the shaft 16 that supports elastic bands used to ligate tissue (see FIG. 4). The body 14 of the endoscope includes a proximal rectangular portion 18 and a distal cylindrical portion 20. Extending laterally from the cylindrical portion 20 is a port 22 that leads to an internal channel (not visible) that extends from the port and through the endoscope body 14 and shaft 16 to the distal tip of the shaft.

The activation portion of the ligator 10 generally comprises a body 24 that includes a mounting arm 26 having a U-shaped bracket 28 that, as depicted in FIG. 1, is adapted to grip the cylindrical portion 20 of the endoscope body 14. The body 24 also includes a nozzle 30 that, as is also depicted in FIG. 1, is adapted to be inserted into the port 22 provided on the cylindrical portion 20 of the endoscope body 14. The body 24 further supports an activation mechanism 32 that can be used to deploy individual elastic bands from the barrel at the distal end of the shaft 16 to perform ligation. As shown in FIG. 1, an activation cord 34 extends from the activation mechanism 32 and through the endoscope channel via the nozzle 30 and the port 22. The components and operation of the activation mechanism 32 are described in detail in relation to FIGS. 2 and 3.

With further reference to FIG. 1, the activation portion of the ligator 10 can further comprise an injection tube 36 that is in fluid communication with the nozzle 30 and, therefore, the endoscope channel, when the nozzle is inserted into the port 22.

Figure 2:
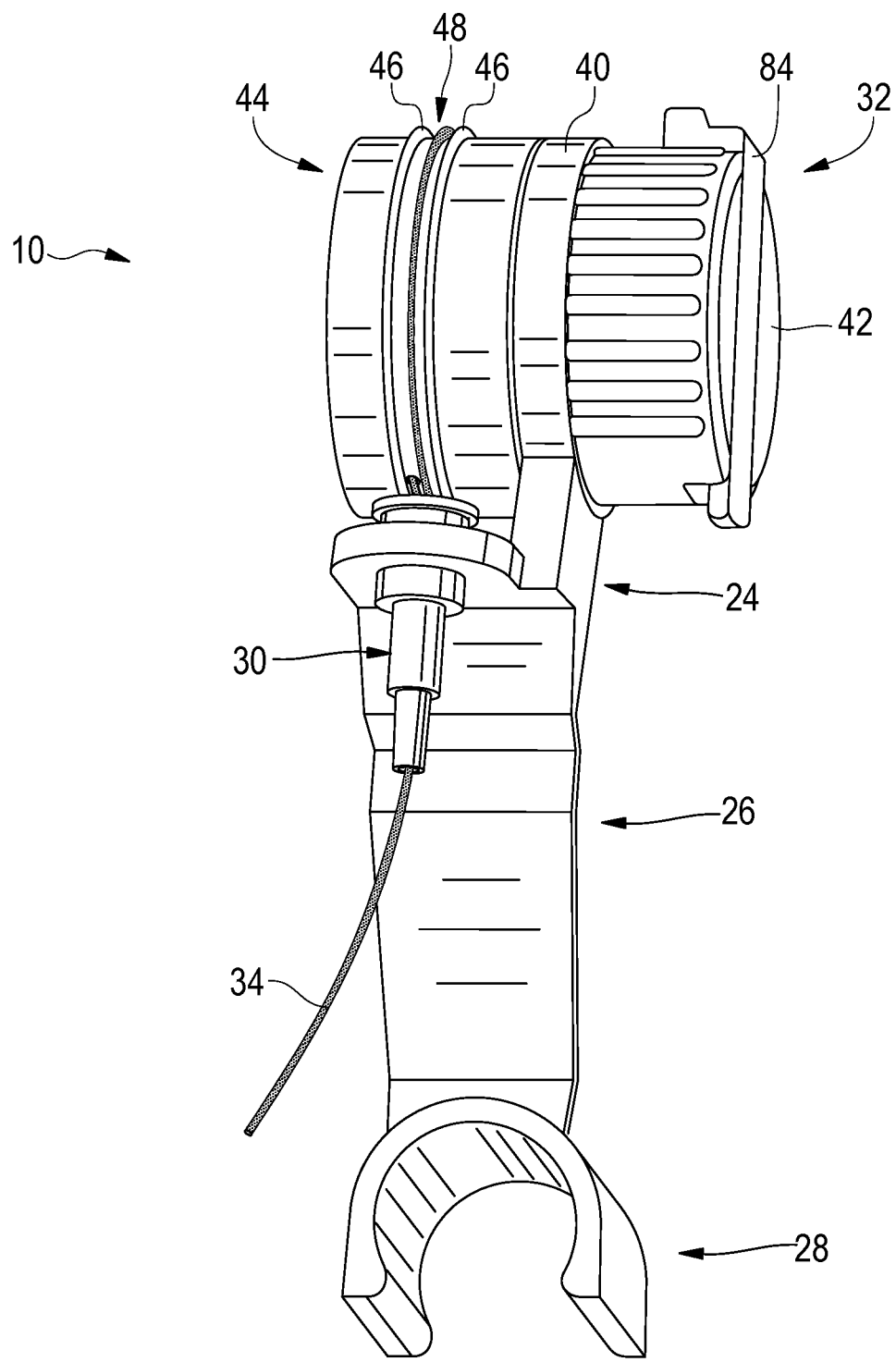
FIG. 2 is a perspective view of the ligator shown in FIG. 1.

FIG. 2 shows the activation portion of the ligator 10 of FIG. 1 separate from the endoscope 12 and in greater detail. As shown in FIG. 2, the body 24 can be unitarily formed from a single piece of material, such as plastic. In addition to the mounting arm 26 and the nozzle 30, the body 24 also includes a circular support hub 40 that supports and forms part of the activation mechanism 32. With further reference to FIG. 2, the activation mechanism 32 also includes an activation knob 42 and a cord winding ring 44. The activation knob 42 is designed to be rotated by the surgeon to deploy individual elastic bands. As is described in relation to FIG. 3, the activation knob 42 can, in some embodiments, be rotated from a start position to an end position beyond which further rotation is not possible. When the activation knob 42 reaches the end position, the activation mechanism 32 causes the deployment of a single elastic band from the barrel at the tip of the endoscope shaft 16. The activation knob 42 can then return to the start position under the force of an internal spring so that it is ready to deploy the next elastic band, if necessary. As indicated in FIG. 2, the activation knob 32 can be generally circular and can include a knurled outer periphery that facilitates gripping by the surgeon.

The cord winding ring 44 comprises a hollow cylindrical ring or tube that includes two continuous circular flanges 46 that together form a cord track 48 into which the activation cord 34 can be wound during operation of the ligator 10. As described below, the cord winding ring 44 can be rotated in a forward (clockwise) direction by rotating the activation knob 42 in a forward (clockwise) direction. Doing so winds the activation cord 34 onto the track 48 of the cord winding ring 44.

Figure 3:
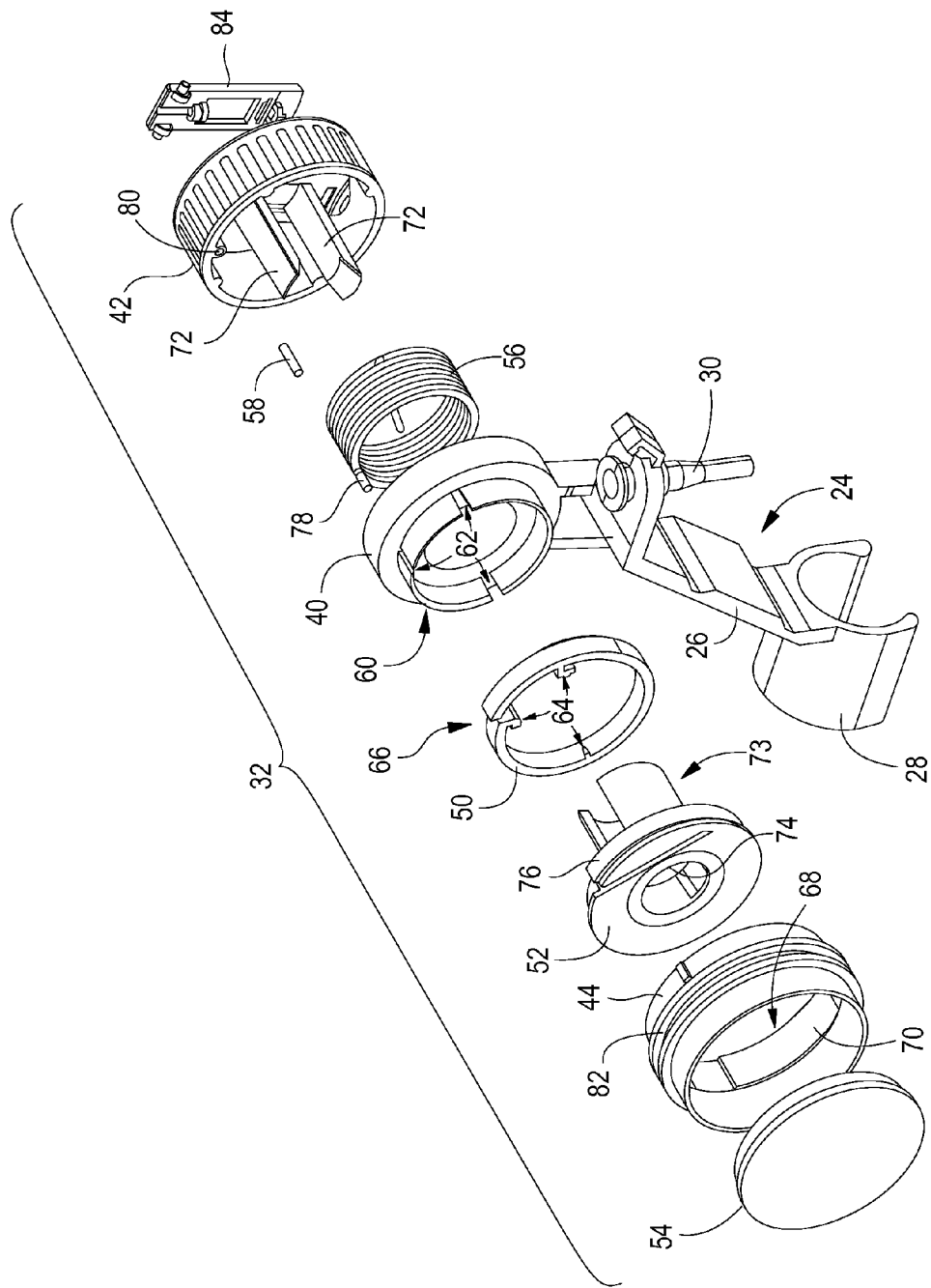
FIG. 3 is an exploded view of an embodiment of an actuation mechanism of the ligator of FIG. 2.

FIG. 3 shows the activation mechanism 32 in an exploded view and, therefore, reveals example internal components of the mechanism. As indicated in this figure, the activation mechanism 32 further comprises a split ring 50, a winding ring driver 52, and an end cap 54 positioned on a first side of the support hub 40, and a torsion spring 56 and a stop element 58 positioned on a second side of the support hub.

The split ring 50 is made of a resilient material that can deform and spring back to its original shape. During assembly, the split ring 50 is mounted on a circular mounting flange 60 that extends laterally from the first side of the support hub 40. As shown in FIG. 3, the mounting flange 60 is discontinuous because it includes multiple slots 62 that are adapted to receive radially extending tabs 64 of the split ring 50. When the split ring 50 is mounted to the support hub 40 with the tabs 64 positioned in the slots 62, the split ring encircles the mounting flange 60 with a free end 66 of the split ring extending radially outward.

Once the split ring 50 is mounted on the mounting flange 60, the cord winding ring 44 can be mounted on the mounting flange over the split ring 50 in a manner in which an internal ratchet surface 68 of the cord winding ring encircles the split ring and its free end 66. The internal ratchet surface 68 comprises multiple (e.g., three) ramps 70 that the stationary free end 66 of the split ring 50 can sequentially travel up as the cord winding ring 44 is rotated in the forward direction. Once the free end 66 reaches the top (tall) end of a ramp 70, it snaps outward into contact with the bottom (low) end of the next ramp. This outward snapping prevents the cord winding ring 44 from traveling in a backward (counterclockwise) direction due to interference between the free end 66 and the previously traveled ramp 70. In addition, the snapping emits an audible click sound that signals to the surgeon that an elastic band has been deployed. With this manner of operation, it can be appreciated that the cord winding ring 44 and the split ring 50 together act as a first ratchet-and-pawl mechanism.

As mentioned above, the cord winding ring 44 can be driven in the forward direction using the activation knob 42. This is possible because the activation knob 42 is mounted to the winding ring driver 52. A shaft 73 of the winding ring driver 52 is adapted to pass through the cord winding ring 44, the split ring 50, and the support hub 40 so as to receive mounting tabs 72 of the activation knob 42, which is positioned on the opposite side of the support hub. More particularly, the mounting tabs 72 are adapted to pass between two halves of the shaft 73 and grip a mounting disc 74 supported between the two halves. When this is achieved, the activation knob 42 and the winding ring driver 52 are secured together and further hold the other components of the activation mechanism 32 together.

With continued reference to FIG. 3, the winding ring driver 52 includes a resilient tab 76. When the winding ring driver 52 and the activation knob 42 are connected in the above-described manner, the ratchet surface 68 of the cord winding ring 44 also encircles the resilient tab 76 of the winding ring driver. When the activation knob 42 is rotated in the forward direction, the distal tip of the tab 76 engages the end of a ramp 70 of the cord winding ring 44 to drive it in the forward direction.

As described above, forward rotation of the activation knob 32 is limited to a designated end position at which a single elastic band is deployed. Once that position is reached, the surgeon can allow the activation wheel to rotate backwards so that it can return to the start position. During this backward rotation, the resilient tab 76 of the winding ring driver 52 travels along the next ramp 70 of the cord winding ring 44 (which cannot rotate backwards and is therefore stationary) until it reaches the top (tall) end of a ramp 70 and snaps outward into contact with the bottom (low) end of the next ramp. At this position, the distal tip of the tab resilient 76 is positioned next to the end of the ramp 70 that it just traveled and the tab can, therefore, drive the ramp (and cord winding ring 44) forward the next time the activation knob 42 is rotated in the forward direction. Upon snapping outward, the resilient tab emits audible click sound that signals to the surgeon that the activation knob 42 has been returned to the start position and that the next elastic band can be deployed, if desired. With this manner of operation, it can be appreciated that the activation mechanism 32 acts as a ratchet mechanism that provides for indexing that divides the rotation of the activation knob into multiple (e.g., 3) indexes.

The torsion spring 56 includes a tang 78 that is received by a hole (not shown) formed in the second side of the support hub 40, while the opposite end of the spring 56 engages the activation knob 42 in a manner in which forward rotation of the knob twists the spring. With such a configuration, the torsion spring 42 biases the activation knob 42 in a rearward direction and opposes forward rotation of the knob. During operation of the activation mechanism 42, the torsion spring 56 serves a return function in which it returns the activation knob 42 to the start position after it has been rotated by the surgeon to the end position. Rotation of the activation knob 42 in both the forward direction (to the end position) and the rearward direction (back to the start position) is limited by the stop element 58, which is mounted in a hole 80 formed in the activation knob. This stop element 58 engages obstructions (not shown) provided on the second side of the support hub 40 at the start and end positions that halt rotation of the activation knob 42. In some embodiments, the stop element 58 comprises a metal (e.g., steel) pin that will not break even if the surgeon attempts to rotate the activation knob 42 beyond either the start or the end position.

With further reference to FIG. 3, the cord winding ring 44 further includes an opening 82 through which the activation cord 34 can pass. The activation cord 34 extends through the activation mechanism 32 to a locking arm 84 on the activation knob 42 that secures the cord to the knob. The locking arm 84 ensures that there is adequate tension in the activation cord 34 prior to firing.

Figure 4:
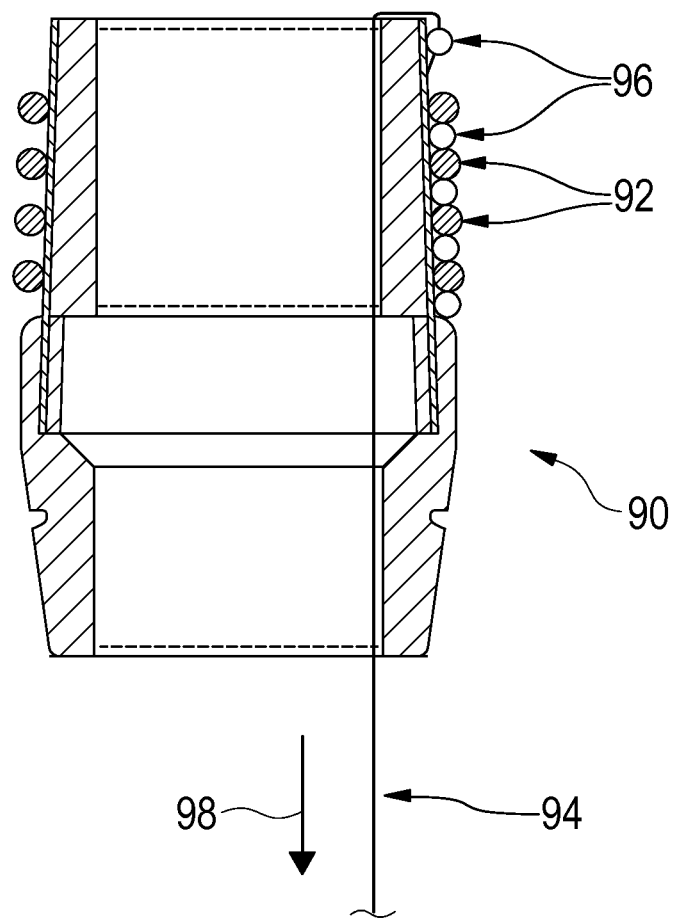
FIG. 4 is a side view of an embodiment of a barrel from which elastic bands can be deployed.

FIG. 4 illustrates a cylindrical barrel 90 that can be mounted to the distal tip of the endoscope shaft 16 shown in FIG. 1. In some embodiments, the barrel 90 has an outer diameter of approximately 13 mm. Mounted on the barrel 90 near its distal end are multiple stretched elastic bands 92 that can be deployed to perform a ligature. As shown in FIG. 4, a deployment cord 94, which can be connected to the activation cord 34, extends through the barrel 90, wraps around the end of the barrel, and passes between the elastic bands 92 and the outer surface of the barrel. As is also shown in FIG. 4, beads 96 are fixedly mounted at discrete locations along the deployment cord 94 with at least one bead being positioned proximal of each elastic band. With such a configuration, individual elastic bands 92 can be pulled off the distal end of the barrel 90 and onto patient tissue when the deployment cord 94 is pulled in the proximal direction indicated by the arrow 98. More particularly, when the activation cord 94 is pulled, the most distal elastic band 92 will be pulled off the end of the barrel 90 because of the presence of one or more of the beads 96.

Figure 5:
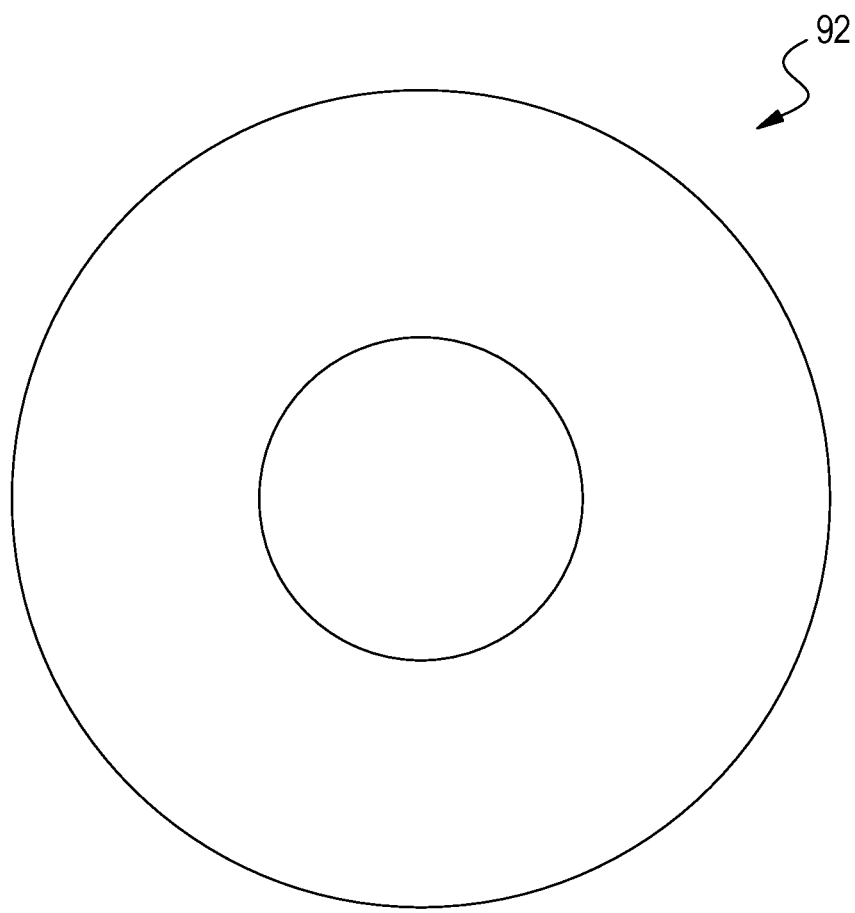
FIG. 5 is a side view of an embodiment of an elastic band that can be used with the barrel of FIG. 4.

FIG. 5 illustrates an example elastic band 92 prior to being stretched to fit around the barrel 90. As shown in this figure, the elastic band 92 can comprise a toroid-shaped body that is unitarily made from a single piece of elastic material. In some embodiments, the elastic material is a synthetic elastomer such as styrene-butadiene rubber, acrylonitrile butadiene rubber, acrylic polymers, synthetic polyisoprene, polyvinyl acetate, or another thermosetting or thermoplastic elastomer. By way of example, the elastic band 92 can have an inner diameter of approximately 1.8 to 3 mm (e.g., 2 mm) and an outer diameter of approximately 4 to 6 mm (e.g., 5 mm). In some embodiments, the elastic band 92 is made using an injection molding process in which elastomer material is injected into a mold. Such a process improves band tolerances, particularly in the case of synthetic elastomer bands.

When the ligator 10 is to be used, the body 24 can be attached to the body 14 of the endoscope 12 in the manner shown in FIG. 1 with the U-shaped bracket 28 gripping the cylindrical portion 20 of the endoscope body and the nozzle 30 inserted into the port 22 of the endoscope body. As indicated in FIG. 1, the activation cord 34 can be threaded through the nozzle 30 and, therefore, can be passed through the port 22 and along the internal channel of the endoscope 12 until the end of the cord emerges from the tip of the endoscope shaft 16. At this point, the end of the activation cord 34 can be secured (e.g., tied) to the end of the deployment cord 94 (FIG. 4) to form a single continuous activation/deployment strand. Once the cords 34, 94 have been connected, the barrel 90 can be attached to the distal tip of the endoscope shaft 16 and slack in the strand can be taken up by rotating the activation knob 42.

The endoscope shaft 16 can next be passed into a cavity of a patient and the optics of the endoscope 12 can be used to locate the tissue that is to be ligated. Once the tissue has been located, it can be drawn into the barrel 90 using a suction force. At this point, one or more elastic bands 92 can be deployed onto the tissue. To do this, the surgeon rotates the activation knob 42 in the forward (clockwise) direction from its start position to its end position against the force of the torsion spring 56. As noted above, doing this causes the cord winding ring 44 to rotate because the activation knob 42 is connected to the winding ring driver 52, which includes a resilient tab 76 that drives an end of a ramp 70 of the cord winding ring. In some embodiments, the activation knob 42 rotates through approximately 120° in traveling from the start position to the end position. Regardless of the particular angle, the activation knob 42 is rotated an amount that results in a length of activation cord 34 being taken up that results in a single elastic band 92 being deployed from the barrel 90.

When the activation knob 42 reaches the end position, the free end 66 of the split ring 50 falls off the top end of a ramp 70 of the cord winding ring 44 and the stop element 58 prevents further forward rotation of the knob. The click sound emitted by the split ring 50 signals to the surgeon that the single elastic band has been deployed. The surgeon can then enable the activation knob 42 to return to the start position under the force of the torsion spring 56. Once the activation knob 42 returns to the start point, the resilient tab 76 of the winding ring driver 52 falls off of the top end of a ramp 70 of the cord winding ring 44 thereby emitting a further click sound that signals to the surgeon that the activation mechanism 32 is prepared to deploy a further elastic band. If the surgeon wishes to deploy one or more other elastic bands 92, he or she can do so by repeating the activation process described above.

The invention claimed is:

1. A ligator adapted for use with an endoscope, the ligator comprising:
   a ligator body adapted to mount to a body of the endoscope;
   a barrel adapted to mount to a distal tip of a shaft of the endoscope, the barrel supporting multiple elastic bands that can be sequentially deployed onto internal tissue; and
   an activation mechanism supported by the ligator body, the activation mechanism including a rotatable activation knob, a rotatable cord winding ring, an activation cord, and a stop element that limits rotation of the activation knob to rotation between a start position and an end position beyond which no further rotation is possible, wherein the activation mechanism further comprises an internal ratchet mechanism including an internal ratchet surface provided in the cord winding ring and an internal resilient element that travels along the ratchet surface during forward rotation of the cord winding ring and prevents backward rotation of the cord winding ring once the end position has been reached, wherein forward rotation of the activation knob causes forward rotation of the cord winding ring and winding of the activation cord onto the cord winding ring, and wherein winding of the activation cord onto the cord winding ring until the end position is reached causes deployment of a single elastic band from the barrel.

2. The ligator of claim 1, wherein the ligator body includes a mounting arm adapted to grip the endoscope body.

3. The ligator of claim 2, wherein it is a U-shaped bracket of the mounting arm that is adapted to grip the endoscope body.

4. The ligator of claim 1, further comprising a deployment cord connected to the activation cord, a portion of the deployment cord being positioned between the elastic bands and an outer surface of the barrel.

5. The ligator of claim 4, wherein the deployment cord comprises multiple beads, at least one bead being positioned proximally of each elastic band.

6. The ligator of claim 1, wherein the elastic bands are synthetic elastomer bands.

7. The ligator of claim 6, wherein the synthetic elastomer bands are made of styrene-butadiene rubber, acrylonitrile butadiene rubber, acrylic polymers, or polyvinyl acetate.

8. The ligator of claim 1, wherein the cord winding ring comprises a winding track into which the activation cord is wound.

9. The ligator of claim 1, wherein the internal ratchet surface of the cord winding ring comprises multiple ramps.

10. The ligator of claim 9, wherein the internal ratchet mechanism further comprises a winding ring driver to which the activation knob is mounted, the winding ring driver including a resilient tab that engages an end of a ramp to drive the cord winding ring forward.

11. The ligator of claim 10, wherein the resilient tab of the winding ring driver snaps outward when it falls off of a ramp and emits an audible click sound that signals to a user that the activation knob has returned to the start position.

12. The ligator of claim 9, wherein the internal resilient element comprises a split ring having a free end that travels upward along the ramps when the cord winding ring is driven forward.

13. The ligator of claim 12, wherein the free end of the split ring snaps outward when it falls off of a ramp and emits an audible click sound that signals to a user that a single elastic band has been deployed.

14. The ligator of claim 1, wherein the activation mechanism further comprises a torsion spring that returns the activation knob to the start position after an elastic band has been deployed.

15. The ligator of claim 1, wherein the stop element is mounted to the activation knob.

16. The ligator of claim 15, wherein the stop element is a steel pin.

* * * * *